United States Patent
Secrist et al.

(10) Patent No.: US 12,245,922 B2
(45) Date of Patent: Mar. 11, 2025

(54) WETNESS INDICATOR FREE FROM HALOGEN-CONTAINING SPECIES

(71) Applicant: Bostik, Inc., Wauwatosa, WI (US)

(72) Inventors: Kimberly E. Secrist, Wauwatosa, WI (US); Neil G. Janetski, Milwaukee, WI (US)

(73) Assignee: Bostik Inc., Wauwatosa, WI (US)

( * ) Notice: Subject to any disclaimer, the term of this patent is extended or adjusted under 35 U.S.C. 154(b) by 855 days.

(21) Appl. No.: 16/816,399

(22) Filed: Mar. 12, 2020

(65) Prior Publication Data

US 2020/0289337 A1  Sep. 17, 2020

Related U.S. Application Data

(60) Provisional application No. 62/818,830, filed on Mar. 15, 2019.

(51) Int. Cl.
| | | |
|---|---|---|
| *A61F 13/42* | (2006.01) | |
| *A61F 13/84* | (2006.01) | |
| *A61L 15/34* | (2006.01) | |
| *A61L 15/56* | (2006.01) | |
| *A61L 15/58* | (2006.01) | |
| *A61F 13/511* | (2006.01) | |
| *A61F 13/514* | (2006.01) | |
| *A61L 26/00* | (2006.01) | |

(52) U.S. Cl.
CPC .......... *A61F 13/42* (2013.01); *A61F 13/8405* (2013.01); *A61L 15/34* (2013.01); *A61L 15/56* (2013.01); *A61L 15/585* (2013.01); *A61F 2013/422* (2013.01); *A61F 2013/426* (2013.01); *A61F 2013/427* (2013.01); *A61F 2013/51165* (2013.01); *A61F 2013/51411* (2013.01); *A61L 26/0071* (2013.01); *A61L 2300/22* (2013.01); *A61L 2300/802* (2013.01)

(58) Field of Classification Search
CPC ................. A61F 13/42; A61F 13/8405; A61F 2013/422; A61F 2013/426; A61F 2013/427; A61L 15/35; A61L 15/56; A61L 15/585; A61L 26/0071; A61L 2300/22; A61L 2300/802
See application file for complete search history.

(56) References Cited

U.S. PATENT DOCUMENTS

| | | | |
|---|---|---|---|
| 4,231,370 A | 11/1980 | Mroz et al. | |
| 4,681,576 A | 7/1987 | Colon et al. | |
| 4,743,238 A | 5/1988 | Colon et al. | |
| 4,895,567 A | 1/1990 | Colon et al. | |
| 5,035,691 A | 7/1991 | Zimmel et al. | |
| 5,342,861 A | 8/1994 | Raykovitz | |

(Continued)

FOREIGN PATENT DOCUMENTS

| | | |
|---|---|---|
| EP | 1330272 A2 | 7/2003 |
| EP | 2067458 B1 | 11/2012 |

(Continued)

*Primary Examiner* — Catharine L Anderson
(74) *Attorney, Agent, or Firm* — Christopher R. Lewis

(57) ABSTRACT

A hot melt wetness indicator comprising an adhesive base composition utilizing a halogen-free species, namely nitrazine yellow, to trigger color change in hygiene articles, such as disposable diapers, to serve as moisture or wetness indicator upon insult. In some embodiments of the invention, the wetness indicator turns from yellow to purple.

21 Claims, 1 Drawing Sheet

Start

After 5min with saline solution

(56) References Cited

U.S. PATENT DOCUMENTS

| | | |
|---|---|---|
| 6,772,708 B2 | 8/2004 | Klofta et al. |
| 6,904,865 B2 | 6/2005 | Klofta et al. |
| 7,159,532 B2 | 1/2007 | Klofta et al. |
| 8,061,292 B2 | 11/2011 | Ahmed et al. |
| 8,828,271 B2 | 9/2014 | Zhang |
| 9,320,824 B2 | 4/2016 | Klofta et al. |
| 9,597,238 B2 * | 3/2017 | Joseph ................ A61F 13/8405 |
| 9,889,222 B2 | 2/2018 | Song |
| 10,759,976 B2 * | 9/2020 | Heacock ................ C08L 1/284 |
| 10,953,129 B2 * | 3/2021 | Corzani ................ B65D 79/02 |
| 2011/0015599 A1 | 1/2011 | Song et al. |
| 2016/0038628 A1 | 2/2016 | Klofta et al. |

FOREIGN PATENT DOCUMENTS

| | | | |
|---|---|---|---|
| JP | H0788128 A | 4/1995 | |
| JP | 2013192888 A2 | 9/2013 | |
| WO | WO9807027 A1 | 2/1998 | |
| WO | 0236177 A2 | 10/2002 | |
| WO | 2016120876 A1 | 8/2016 | |

* cited by examiner

Start · After 5min with saline solution

Start · After 5min with saline solution

Start · After 5min with saline solution

Start · After 5min with saline solution

WETNESS INDICATOR FREE FROM HALOGEN-CONTAINING SPECIES

FIELD OF THE INVENTION

The invention relates to a hot melt wetness indicator adhesive composition that can be used in disposable nonwoven absorbent articles, such as diapers. The indicator adhesive will indicate wetness when body fluid is discharged from the wearer by changing from a first color to a second color (or from colorless to a color) without the use of halogen-containing compounds.

BACKGROUND OF THE INVENTION

Disposable nonwoven absorbent products have widespread acceptance for infant, young child, and incontinent adult care applications. Typical disposable nonwoven absorbent articles include diapers, training pants, adult incontinent pads and briefs, feminine sanitary napkins or pads and tampons. Disposable nonwoven absorbent articles such as those mentioned function to receive and contain urine and other body fluids that the wearer secretes. These items are worn against or in close proximity to the skin of the wearer.

Typical disposable nonwoven absorbent articles consist of a fluid—impervious film back sheet, a porous fluid permeable nonwoven top sheet, and an absorbent core sandwiched between the top and back sheets. These articles are usually bonded using hot melt adhesives and do not require the indicating strip to further bind the film and nonwoven components together. In addition to this basic construction, these absorbent articles usually have many other features to either improve the body fluid containment function or to enhance the comfort level for the wearer. For example, infant diapers contain elastic leg cuffs attached to the top sheet for enhanced fluid containment.

Since disposable nonwoven absorbent articles are widely used for body fluid containment function, it is desirable to know whether the article is wet and thus requires replacement. Monitoring of wetness by internal visual inspection can be time consuming and unpleasant. It is therefore invaluable to incorporate a function to signal wetness, visible externally, into a disposable nonwoven absorbent article such as a diaper.

Approaches using coating stripes of wetness indicator adhesives, or wetness indicators to signal wetness by way of color change have been described in Mroz et al., U.S. Pat. No. 4,231,370. This patent discloses an improved absorbent product having a wetness indicator disposed between a translucent cover member and an absorbent member. According to the disclosure, the wetness indictor is applied in the form of a stripe to a portion of the inwardly facing surface of a back sheet of a disposable diaper. Such a wetness indictor contains a pH—change/color—change type of colorant dispersed in water-based adhesive latexes of styrene/2-ethylhexylacrylate copolymer, ethylene/vinyl acetate copolymer, or polyvinyl acetate. The indicator adheres to the back sheet and dries to a flexible coating that is yellow in color. When insulted by body secretions such as urine, the indicator changes from yellow to blue, signaling the presence of moisture. To obtain a suitable pH, sufficient acid buffering means such as phosphoric acid must be added to the latexes. Phosphoric acid is a harsh acid, which could raise safety concerns. Another disadvantage of this patent is that the means of water or solvent removal has to be provided during manufacturing.

Colon et al., U.S. Pat. Nos. 4,681,576, 4,743,238 and 4,895,567, disclose hot melt wetness indicator adhesives that change color upon insult with urine or water. These adhesives are based on a water-soluble polyvinyl pyrrolidone polymer, or a water soluble vinyl pyrrolidone-vinyl acetate copolymer, or an ethylene-acrylic acid copolymer in combination with a fatty acid and a wetness indicating dye. The composition can contain a variety of other ingredients such as water-soluble waxes, glycerol esters, ethylene-vinyl acetate copolymers and hydrogenated oils.

Zimmel et al., U.S. Pat. No. 5,035,691, disclose a hot melt wetness indicator composition based on an adduct which is prepared by reacting ethylene-acrylic acid copolymer with polyethylene oxide under monobutyl tin (IV) oxide catalyst. The composition contains 0.03 to 0.5 wt % acid-base indicator as the active ingredient to signal the presence of moisture.

Raykovitz, U.S. Pat. No. 5,342,861, discloses a composition similar to that of Zimmel et al. in that the composition comprises a wetness indicating agent such as a pH indicator, a graft copolymer prepared by reacting a vinyl polymer with low molecular weight polyethylene oxide, and a compatible tackifier.

Nitrazine yellow has been used as a wetness indicator for indicating that a diaper has been insulted with urine. For example, Habji et al., International Patent Application No. WO 2016/120876, describe a design for a wetness indicator in a diaper that allows someone to observe color change without removing clothing; the wetness indicator sticks out in the form of an extending tab. The nitrazine yellow is dissolved in a solvent, such as methanol, and then dried onto a gauze or substrate, serving as the tab.

Klofta et al., U.S. Patent Application Publication No. 2016/0038628, discloses a wetness indicating agent which may be in the form of a hot melt adhesive. Klofta et al. require not only a pH indicator (such as nitrazine, among a long list of possibilities), but also require the use of a permanent dye for the wetness indicator to function properly. Furthermore, Klofta et al. do not contemplate the use of polyethylene glycol as either the sole base polymer or one of the base polymers.

Song et al., U.S. Pat. No. 9,889,222, disclose an aqueous medium-sensitive coating composition which is affixed to an absorbent article adjacent a longitudinally directed side peripheral edge. The coating composition includes a betaine ester or betaine ester derivative having a functional active group derived from a fragrance with a hydroxyl group, a color changing visual indicator chemistry, where the visual indicator chemistry is selected from at least one of the group of a pH indicator dye and pH adjuster, a thermochromic dye, and a polarity-sensitive dye.

Unlike the prior art, the invention as described here required advanced knowledge of wetness indicator technology and incorporates an uncommon pH indicator to allow for a wetness indicator free from potentially harmful halogen-species. Finally, the above prior art merely mentions the use of nitrazine as a pH indicator amid a large listing of other pH indicators that are unlikely to function in this application.

Klofta et al., U.S. Pat. No. 9,320,824 disclose a liquid-activated formulation in a solvent-based binding matrix, for use as wetness/fluid indicators in absorbent articles. The formulation comprises a liquid-activated colorant, a hydrochromic ionic compound, an opacifier, and a solvent-based binding matrix.

SUMMARY OF THE INVENTION

The prior art compositions herein mentioned above have several deficiencies. The hot melt wetness indicator composition disclosed in Colon et al, for example, exhibits poor thermal stability. Thus, when heated at elevated temperatures between 250-300° F., which is typically encountered during hot melt application, the adhesives can severely degrade as manifested by char, skin formulation, and color darkening. Most of the components in Colon's composition are incompatible with each other, and therefore, the composition can suffer from phase separation during application at the typical hot melt adhesive coating conditions. Other deficiencies are the poor environmental stability and poor bleed-through or wash-out resistance. In some cases, the coated indicator tends to change slowly and prematurely from yellow to green and finally to blue from exposure to atmospheric moisture during storage. This aspect is particularly important since finished nonwoven adsorbent products can be stored for a few months before they reach consumer's hands, and in relatively hot and humid environments. A premature color change during storage will render the product useless. An additional deficiency is the poor intensity of color change of the indicator when insulted, resulting in the color change being barely visible through translucent substrates. The compositions taught by Zimmel et al. and Raykovitz, on the other hand, necessitate harsh conditions to carry out chemical grafting of low molecular weight hydrophilic PEG to another relatively high molecular weight hydrophobic polymer. Their grafting reactions require either an organotin catalyst (Zimmel) or a peroxide initiator (Raykovitz). Problems can arise from product safety concerns with residual organotin compounds and peroxides. Since the hydrophilic PEG is typically incompatible with the vinyl polymer used for preparation of the graft copolymer, the unreacted reactants can pose compatibility problems for the final wetness indicator composition.

In view of the deficiencies of the prior art products and a market perception to avoid any halogens in hygiene articles, needs exist for a new wetness indicator that is compatible, that is thermally and environmentally stable, that has intense color change and good wash-out resistance, that can withstand multiple insults during use, that is easy to manufacture and apply, and that is free from halogen-containing species. Furthermore, it is especially preferable to select a pH indicator and a formulation such that the color of the wetness indicator undergoes a pronounced color change, such as yellow to blue or, more preferably, from yellow to purple, upon insult.

The present invention is directed towards a wetness indicator composition (also referred to as a hot melt wetness indicator or a hot melt wetness indicator (or indicating) adhesive composition) comprising an adhesive base composition incorporating a halogen-free pH wetness indicator consisting of nitrazine yellow. In one embodiment, the adhesive base composition may be composed of water soluble, or at least partially water soluble, components, and in another embodiment the adhesive base composition may be composed of water sensitive components as for example one or more water insoluble polymers and a surfactant.

Preferably the adhesive is a hot melt adhesive. Hot melt adhesives are preferred over other types of adhesives for many reasons. Unlike water-based or solvent-based adhesives, there is no liquid carrier that needs to be evaporated. Hot melts are applied in a molten state and solidify when cooled. Thus, they can be applied at much faster line speeds since no drying needs to occur. Hot melts also tend to stay in place better since they stop flowing as soon as they cool. This is important when trying to extrude or print a pattern of adhesive.

In one embodiment, the wetness indicator is based on an at least partially water soluble hot melt adhesive base which includes a polymer that may be a homopolymer, copolymer, terpolymer, interpolymer or blends thereof together with a tackifying resin, a stabilizer, and a halogen-free pH indicating agent, namely nitrazine yellow, which changes color (or goes from pale or colorless to a color) in response to changes in pH when contacted by a liquid such as urine. The composition of the present invention has overcome the deficiencies of the prior art wetness indicators. One embodiment of the present invention is to provide a wetness indictor that has excellent heat and environmental stability, improved fastness, vivid color change, easy manufacturing, and easy application.

The hot melt wetness indicator composition of the present invention can be applied using a variety of conventional coating techniques known in the art. It is especially suited for slot coating, multibeads, spiral spray, and different variations of melt-blown coatings. The hot melt wetness indicator could be applied in a way to create patterns, letters, or pictures.

The preferred wetness indicator adhesive composition of the present invention is a hot melt adhesive composition that comprises as ingredients thereof a mixture of the following components:
(a) about 1 to about 80% by weight of a base polymer, preferably in an amount between about 1 and about 45% by weight, and most preferably between about 1% and 35% by weight;
(b) about 15 to about 75% by weight of a tackifier preferably in an amount between about 20 and about 70% by weight, preferably between about 20% and 50% by weight;
(c) a pH adjuster in an amount sufficient to cause the pH of the composition to be less than 6, preferably between 4 and 6, more preferably between 5 and 6, and most preferably between 5.5 and 6; and
(d) about 0.1 to about 5% by weight of a pH indicating agent consisting of nitrazine yellow.

As used herein, when a single component is identified (e.g., a base polymer), the composition could include either a single one of that component or a mixture of such components. Optional additional ingredients include:
(a) a surfactant or combination of surfactants in the amount of about 1% to 30% by weight, and preferably in the amount of about 4-15% by weight;
(b) a plasticizer in the amount of about 1-15% by weight, preferably in the amount of about 1% to 10% by weight, most preferably in the amount of about 1% to 7% by weight;
(c) about 0.1-5% by weight of one or more of a stabilizer or antioxidant;

The adhesive may contain other conventional ingredients such as a filler or a wax. In an embodiment of the invention, the pH adjuster is present in an amount between about 5 and about 55% by weight, preferably between about 10% and 50% by weight, and most preferably between about 19 and 43% by weight.

As a hot melt adhesive, the composition does not require water or solvent formulation to be evaporated upon application to the article. In an embodiment of the invention, the hot melt wetness indicator is not formed on a separate tab which extends beyond the structure of the diaper. In addition, the formulation of the present invention, using nitrazine yellow as the indicator does not require the use of either a permanent dye or a fluorescing agent, or both, to function properly. According to another embodiment, the hot melt wetness indicator composition does not include a wax, and more preferably does not include a polyethylene glycol wax, and/or includes polyethylene glycol as either the sole base polymer or one of the base polymers. According to another embodiment of the invention, the hot melt wetness indicator composition does not include a compound which releases a functional group having a fragrance upon insult with urine. More specifically, the hot melt wetness indicator composition of the invention does not include a betaine ester or a betaine ester derivative. According to still another embodiment, hot melt wetness indicator composition does not contain a reactive ionic compound, such as an ionizing salt. Finally, the hot melt wetness indicator need not be formed into or as part of a strip of paper or dissolved onto a sensor.

According to an embodiment of the invention, the hot melt wetness indicator composition consists essentially of or consists of a base polymer, a tackifier, a pH adjuster, a pH indicating agent and, optionally at least one of an antioxidant or a plasticizer. According to another embodiment of the invention, the hot melt wetness indicator composition consists essentially of or consists of a base polymer, a tackifier, a pH adjuster, a pH indicating agent and an antioxidant and optionally at least one of a wax, a filler, a stabilizer, surfactant, and a plasticizer.

According to another embodiment of the invention, a hot melt wetness indicator composition comprises about 1 to about 80% by weight of a base polymer; about 15 to about 75% by weight of a tackifier; a pH adjuster in an amount sufficient to cause the pH of the composition to be less than 6, preferably between 4 and 6, more preferably between 5 and 6, and most preferably between 5.5 and 6; and about 0.01 to about 5% by weight of a pH indicating agent consisting of nitrazine yellow.

According to another embodiment of the invention, a hygience article comprises a fluid-impervious back sheet having an inner surface, a nonwoven top sheet, and an absorbent core disposed between the back sheet and the top sheet; and a hot melt wetness indicator bonded to the inner surface of the back sheet and in contact with the absorbent core such that, upon insult of the absorbent core with urine, the urine contacts the hot melt wetness indicator, wherein the hot melt wetness indicating composition comprises: about 1 to about 80% by weight of a base polymer; about 15 to about 75% by weight of a tackifier; a pH adjuster in an amount sufficient to cause the pH of the composition to be less than 6, preferably between 4 and 6, more preferably between 5 and 6, and most preferably between 5.5 and 5; and about 0.01 to about 5% by weight of a pH indicating agent consisting of nitrazine yellow.

Other features and advantages of the invention may be apparent to those skilled in the art upon reviewing the following drawings and description thereof.

DETAILED DESCRIPTION OF THE INVENTION

Figure 1A:
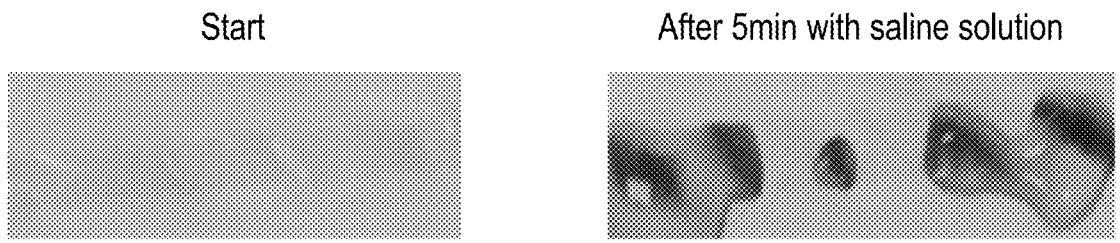
FIGS. 1(a) to 1(d) show four wetness indicators of the present invention before and after insult with saline solution.

In accordance with the present invention, a hot melt wetness indicator is formulated by mixing about 1 to 80% by weight of a base polymer component; about 15 to 75% by weight of a compatible tackifier; a pH adjuster in an amount sufficient to cause the pH of the composition to be less than 6, preferably between 4 and 6, more preferably between 5 and 6, and most preferably between 5.5 and 6; and about 0.01 to about 5% by weight of a pH indicating agent consisting of nitrazine yellow. Other optional ingredients can be added to modify or enhance the physical and performance characteristics of the composition. Such optional ingredients include a surfactant, a plasticizer, a stabilizer or antioxidant, a filler, and a wax.

Any of a variety of available thermoplastic materials can be used, either alone or as a blend, as the base polymer ingredient in the compositions of the invention. With respect to the adhesive composition, the polymer may be a homopolymer, a copolymer, a terpolymer, an interpolymer, or blends thereof, and may be present in an amount from about 1% to about 80% by weight, preferably from about 1 and about 45% by weight, preferably between about 1% and 40% by weight. Examples of such thermoplastic materials include ethylene based polymers, including ethylene/vinyl acetate (EVA), ethylene acrylate, ethylene methacrylate, ethylene methyl acrylate, ethylene methyl methacrylate, high and low density polyethylene, polyethylene blends and chemically modified polyethylene, copolymers of ethylene and 1-6 mono- or di-unsaturated monomers, ethylene/styrene interpolymers (ESI), polyesters such as sulfonated polyesters; amorphous polyalphaolefins (APAOs), including atactic polypropylene, and others; metallocene catalyzed polyalphaolefins; SIS (styrene-isoprene-styrene) block copolymer; SBS (styrene-butadiene-styrene) block copolymer; SEBS (styrene-ethylene-butylene-styrene) block copolymer; SEEPS (styrene-ethylene/ethylene-propylene styrene) block copolymer; SBR (styrene-butadiene-rubber); acrylic polymers and copolymers; as well as styrene acrylic polymers and copolymers; polybutene-1 homopolymers and copolymers, commonly referred to as polybutylene, linear A-B-A block, linear A-(B-A)n-B multiblock copolymers, and radial or teleblock copolymers of the formula (A-B)n-Y wherein A comprises a polystyrene block, B comprises a substantially rubbery polybutadiene or polyisoprene block, Y comprises a multivalent compound, and n is an integer of at least 3. The midblocks can be post-treated to improve their heat stability through hydrogenation or other post-treatment removing residual unsaturation. The size and the amount of the A or end blocks in the A-B-A block copolymer structure may be as much as 14-51 wt-% of the polymer.

In addition, water soluble polymers may also be employed as the thermoplastic material. Common water soluble polymers include polyesters such as sulfonated polyesters, polyvinyl methyl ether, polyalkyleneimine polymers and copolymers, polyvinyl alcohol, polylactide polymers, polyethylene glycol polymers, polyacrylic acid and salts thereof, ethylene/acrylic acid and salts thereof, polyvinylpyrrolidone, and polyvinylpyrrolidone/vinyl acetate. Other water soluble polymers may be used depending upon the desired end use and properties of the polymer, and thus the above list should neither be considered all-inclusive nor limiting on the scope of the term "thermoplastic material" or "thermoplastic polymer" as used herein.

In an embodiment, the base polymer comprises, consists essentially of, or consists of polyethylene glycol. In another embodiment, the base polymer comprises, consists essentially of, or consists of polyethylene glycol, preferably in an amount of between about 10 and about 55% by weight, preferably between about 20 and 45% by weight, and most preferably between about 25 and 40% by weight. Preferably, the molecular weight of the polyethylene glycol is between about 10,000 and about 40,000 daltons, preferably between about 12,000 and about 35,000 daltons, and most preferably between about 15,000 and 20,000 daltons. As used herein, "molecular weight" refers to weight average molecular weight and is determined by gel permeation using polystyrene standards.

In an embodiment using polyethylene glycol as the sole base polymer, it has surprisingly been found that the wetness indicator turns purple upon insult. It is believed that at least one of the following factors, in combination with the presence of polyethylene glycol, leads to the wetness indicator turning purple: polyethylene glycol present in the formulation in an amount of about 15 to about 45% by weight; isostearic acid present in the formulation; isostearic acid present in the formulation in an amount of from about 0.5 to about 7% by weight; isostearic acid present in the formulation along with stearic acid; isostearic acid present in the formulation along with stearic acid in a weight ratio range of isostearic:stearic of 1:40 to 1:2; a combination of a hydrogenated rosin such as Foral AX-E and C9 hydrocarbon resin such as Hikotack DP-100 present in the formulation as a tackifier; or any combination of any of these factors.

The tackifying resins which are used in the hot melt adhesives of the present invention are those which extend adhesive properties and improve specific adhesion. As used herein, the term "tackifying resin" includes:
a. natural and modified rosin such as, for example, gum rosin, wood rosin, tall-oil rosin, distilled rosin, hydrogenated rosin, dimerized rosin and polymerized rosin;
b. glycerol and pentaerythritol esters of natural and modified rosin, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall-oil rosin, and the phenolic modified pentaerythritol ester of rosin;
c. polyterpene resins having a softening point, as determined by ASTM method E28-58T, of from about 20° C. to 140° C., the latter polyterpene resins generally resulting from the polymerization of terpene hydrocarbons, such as the monoterpene known as pinene, in the presence of Friedel-Crafts catalysts at moderately low temperatures; also included are the hydrogenated polyterpene resins;
d. copolymers and terpolymers of natural terpenes, e.g. styrene/terpene, α-methyl styrene/terpene and vinyl toluene/terpene;
e. phenolic-modified terpene resins such as, for example, the resin product resulting from the condensation, in an acidic medium, of a terpene and a phenol;
f. oligomeric amide ester resin such as, for example, Unirez 2620 from Arizona Chemical;
g. aliphatic petroleum hydrocarbon resins having Ring and Ball softening points of from about 10° C. to 140° C., the latter resins resulting from the polymerization of monomers consisting primarily of olefins and diolefins; also included are the hydrogenated aliphatic petroleum hydrocarbon resins; examples of such commercially available resins based on a C5-olefin fraction of this type are "Wingtack 95" and "Wingtack 115" tackifying resins sold by Cray Valley US;
h. aromatic petroleum hydrocarbons and the hydrogenated derivatives thereof; and
i. aliphatic/aromatic petroleum derived hydrocarbons and the hydrogenated derivatives thereof (e.g., aromatic hydrocarbon resins).

Mixtures of two or more of the above described tackifying resins may be used for some formulations. Although a range of 15-75% by weight tackifying resin may be used, the preferred range is between about 20 and about 70% by weight, preferably between about 20% and 50% by weight. An example of a commercially available tackifying resin which is useful for the present invention includes the resin which is identified commercially by the trade designation Sylvalite RE 100L. This resin is a pentaerythritol based tall-oil rosin ester, and Sylvalite RE 85L, a glycerol ester of tall oil rosin, both are available from Arizona Chemical Company.

Commercially available polymerized and modified rosins may be secured from Arizona Chemical Company under the trade designations "Sylvaros PR R, PR R85, and Uni-Tac 70," respectively. Commercially suitable partially hydrogenated rosins may be available from Eastman Chemical Company under the trade designations "Foral AX," "Foral AXE," and "Stabelite."

The hot melt wetness indicator composition of the present invention also includes a pH adjuster such that pH is maintained at a certain level prior to exposure to aqueous-based bodily fluids. In particular, the pH adjuster is present in an amount sufficient to cause the pH of the composition to be less than 6, preferably between 4 and 6, more preferably between 5 and 6. Upon exposure to such soiling by bodily fluids, the pH of the substrate with coating will change, thereby triggering the color changing effect. The pH adjuster is any molecule or composition that may be used to control the pH of the color changing composition. The pH adjuster may be an acid, a base or a combination of both such as would be found with a buffering composition. The pH adjuster is selected in conjunction with nitrazine yellow, which is used herein as the pH indicating agent. The pH adjuster serves to render the pH of the hot melt wetness indicator to a range over which nitrazine yellow retains its yellow color.

Examples of suitable acid pH adjusters include organic acids, inorganic acids and polymeric acids; more specifically, examples of such acids include organic acids include glycolic acid, citric acid, lactic acid, ascorbic acid, oxalic acid, maleic acid, tartaric acid, salicylic acid, palmitic acid, stearic acid, and isostearic acid, and mixtures thereof. Further examples organic acids include polyacrylic acids, polymethacrylic acids and copolymers containing acrylic acids, methacrylic acids or both acrylic acids and methacrylic acids. In certain embodiments, the pH adjuster comprises, consists essentially of, or consists of stearic acid, isostearic acid or a mixture thereof.

The amount of the pH adjusters depends on the pH of the composition without the pH adjuster and the strength of the pH adjuster. In some embodiments, the pH adjuster is present in an amount between about 5 and about 55% by weight, preferably between about 10% and 50% by weight, and most preferably between about 19 and 43% by weight. Further examples of pH adjusters may be found in US 2011/0015599 to Song et al., which is incorporated herein by reference in its entirety.

The hot melt wetness indicator composition of the present invention also includes a pH indicating agent consisting of nitrazine yellow. The amount of pH indicating agent is that amount needed to readily show a color change upon insult with urine. Typically, it is present in amounts of about 0.05 to 5% by weight, preferably in an amount between about 0.1 and about 2.5% by weight, most preferably between about 0.15% and 1.5% by weight. Nitrazine yellow undergoes a color change from yellow to blue as the pH changes from less than 6 to above 6, most notably above 7.2. The hot melt wetness indicator is caused to have a pH above 6 by the interaction of urine and the composition. Such a pH is created in the hot melt indicator as moisture permeates the hydrophilic organic matrix.

Figure 1B:
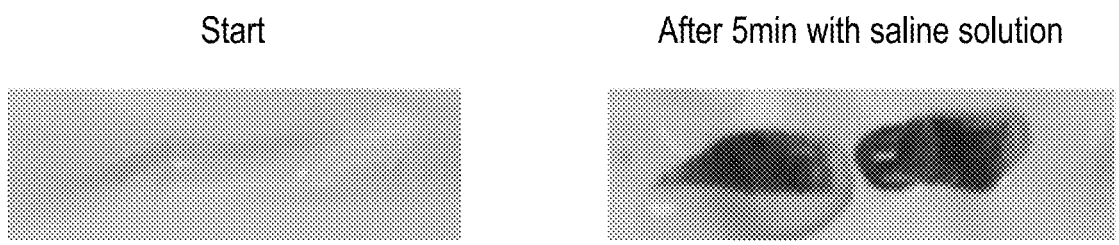
Figure 1C:
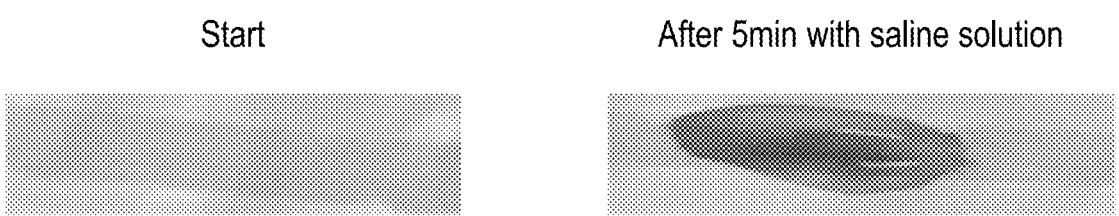
Figure 1D:
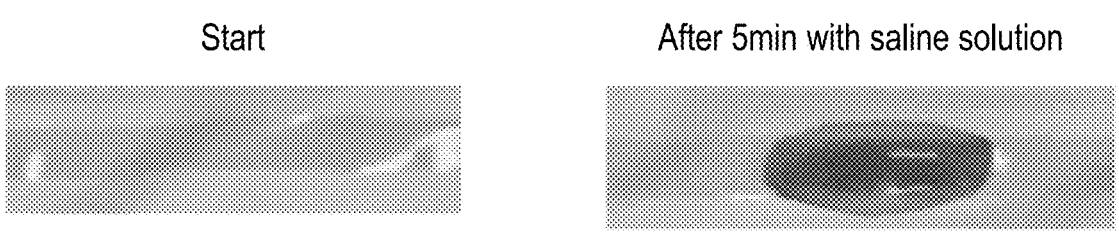

The pH indicating agent produces a visual signal perceptible to the human eye under visible light to indicate that the absorbent article has been wetted with urine. The visual signal is a change in color, such as from yellow, orange, or pink to blue or purple, or a change from colorless or essentially colorless to a color, such as colorless to blue or purple. The pH indicating agent is used in an amount effective to provide the composition with a readily visible color change (or color, if the initial condition was colorless) when wet that is distinguishable from the color of the dry composition. Particularly desirable initial (before color change) starting colors include colorless, yellow, orange, green, tan, and shades and combinations thereof. Desirable final colors (after change) are preferably noticeably different from the initial color. Preferred colors typically include blue, purple, and shades thereof. FIGS. 1(a) to 1(d) described below demonstrate some of the possible initial and final colors possibilities.

The present invention may include a stabilizer or antioxidant in an amount of from about 0% to about 5% by weight. Preferably from about 0.1% to 1% of a stabilizer is incorporated into the composition. The stabilizers which are useful in the hot melt wetness indicator adhesive compositions of the present invention are incorporated to help protect the polymers noted above, and thereby the total adhesive system, from the effects of thermal and oxidative degradation which normally occurs during the manufacture and application of the indicator as well as in the ordinary exposure of the final product to the ambient environment. Among the applicable stabilizers are high molecular weight hindered phenols and multifunction phenols, such as sulfur and phosphorous-containing phenols. Hindered phenols are well known to those skilled in the art and may be characterized as phenolic compounds that also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl)benzene;
pentaerythritol tetrakis-3(3,5-di-tert-butyl-4-hydroxyphenyl) propionate;
n-octadecyl-3(3,5-di-tert-butyl-4-hydroxyphenyl) propionate;
4,4'-methylenebis(4-methyl-6-tert butylphenol);
2,6-di-tert-butylphenol;
6-(4-hydroxyphenoxy)-2,4-bis(n-octylthio)-1,3,5-triazine;
2,3,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate; and
sorbitol hexa-3(3,5-di-tert-butyl-4-hydroxy-phenyl) propionate.

Especially preferred as a stabilizer is pentaerythritol tetrakis-3(3,5-di-tert-butyl-4-hydroxyphenol) propionate.

The performance of these stabilizers may be further enhanced by utilizing, in conjunction therewith; (1) synergists such as, for example, thiodipropionate esters and phosphites; and (2) chelating agents and metal deactivators such as, for example, ethylenediaminetetraacetic acid, salts thereof, and disalicylalpropylenediimine.

The wetness indicator composition of the present invention may also contain from about 1 to 30% by weight, and preferably about 1% to 15% by weight, of a surfactant to make the adhesive more hydrophilic and to impart water permeability to the composition. The surfactants suitable for use herein comprise cationic, anionic or nonionic types with the nonionic type preferred. The more preferred surfactant is selected from a group of nonionic surfactants having HLB less than 15. These surfactants include alkyl amines and amides; alkanolamines and amides; amine oxides; ethoxylated fatty alcohols, ethoxylated fatty acids, ethoxylated alkylphenols, ethoxylated amines or amides; ethoxylated fatty esters and oils; glycerol fatty esters and their ethoxylated derivatives; sorbitan derivatives; sucrose and glucose esters and their derivatives. The most preferred surfactants will have a HLB between 3 and 12 and are selected from a subgroup including ethoxylated fatty alcohols, ethoxylated fatty acids, stearic acid, glycerol esters of fatty acids and their derivatives and sorbitan derivatives. Mixtures of two or more surfactants herein described above may be used for some formulations.

As used herein, the term "surfactant" or "surface-active agent" refers to any compound that reduces surface tension when dissolved in water or water solutions, or which reduces interfacial tension between two liquids, or between a liquid and a solid. Examples of suitable surfactants include, but are not limited to, the following:

a. Fatty acid esters such as glycerol esters, PEG esters, and sorbitan esters, including ethylene glycol distearate, ethylene glycol mono stearate, glycerol mono and/or dioleate, PEG dioleate, PEG monolaurate, sorbitan monolaurate, sorbitan trioleate, etc. These surfactants are available from ICI, Rhone-Poulenc, and other sources.

b. Nonionic ethoxylates such as alkylphenol ethoxylates, alcohol ethoxylates, alkylamine ethoxylates, etc., including octylphenol ethoxylate, nonylphenol ethoxylate, alkylamine ethoxylates, etc. These surfactants are available from Rhone-Poulenc, Union Carbide, and other sources.

c. Nonionic surfactants such as 2,4,7,9-tetramethyl-5-decyn-4,7-diol available from Air Products.

d. Ethylene oxide/Propylene oxide copolymers which are available from Union Carbide, BASF, etc. It should be noted that these and other surfactants can be blended if necessary to produce the best blend of hydrophilic performance properties.

Atmer 129, a glycerol monostearate, manufactured by Uniquema Corporation, Atmer 688, a nonionic surfactant blend manufactured by ICI Americas, Inc., and Aerosol OT 100% surfactant (dioctyl sodium sulfosuccinate) made by Cytec Industries, Inc. have been found to be preferred surfactants for use in the present adhesive composition.

Optionally, the hot melt wetness indicator composition may also contain a plasticizer. Both water soluble and water insoluble plasticizers can be present in the composition of the present invention either alone or in any desired combination in amounts of about 1% to about 50% by weight, preferably from about 5% to about 40% by weight, and most preferably from about 20% to about 35% by weight, in order to provide desired viscosity control without substantially decreasing the adhesive strength or the service temperature of the adhesive. Both liquid and solid plasticizers can be used in the composition of the present invention.

The water soluble plasticizers used herein comprise low molecular weight polyethylene glycols, multifunctional alcohol, and the general class of surfactants wherein the molecules contain both a hydrophilic group and a hydrophobic group. The hydrophilic group of the molecule generally consists of, but is not limited to, polyethylene glycol, polypropylene glycol, a mono- or di-hydroxylated amino group, an ethoxylated amino radical, polyalkylene glycol esters of carboxylic group, substituted or unsubstituted glycerol, glucose, sucrose and sorbitan groups. The hydrophobic group of the molecule generally consists of, but is not limited to, a hydrocarbon radical such as, alkylphenol groups, dialkyl phenol groups, or a linear or branched aliphatic radicals. The preferred soluble plasticizers include ethoxylated alkyphenols, ethoxylated fatty acids and ethoxylated fatty alcohol having a HLB value in the range of 8.0-20.0. An ethoxylated alkyphenol with HLB value of 13.5 can be obtained under the trade designation Triton X-100 from Union Carbide Corporation of Danbury, Conn., and water soluble ethoxylated fatty acids, such as polyethylene glycol 600 monolaurate (HLB=14.6) and polyethylene glycol 1000 dilaurate (HLB=14.2), can be purchased from Stepan Company of Northfield, Ill. under the trade designations of Kessco PEG 600MC and PEG 1000DL, respectively.

A suitable water insoluble plasticizer may be selected from the group which includes dipropylene glycol dibenzoate, pentaerythritol tetrabenzoate; polyethylene glycol 400-di-2-ethylhexoate; 2-ethylhexyl diphenyl phosphate; butyl benzyl phthalate, dibutyl phthalate, dioctyl phthalate, various substituted citrates, and glycerates. Suitable dipropylene glycol dibenzoate and pentaerythritol tetrabenzoate may be purchased from Velsicol Chemical Company of Chicago, Ill. under the trade designations "Benzoflex 9-88 and S-552", respectively. Further, a suitable polyethylene glycol 400-di-2-ethylhexoate may be purchased from C.P. Hall Company of Chicago, Ill. under the trade designation "Tegmer 809". A suitable 2-ethylhexyl diphenyl phosphate, and a butyl benzyl phthalate may be purchased from Monsanto Industrial Chemical Company of St. Louis, Mo. under the trade designation "Santicizer 141 and 160", respectively.

A suitable plasticizer may be selected from the group which not only includes the usual plasticizing oils, such as mineral oil, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animal oils include glycerol esters of the usual fatty acids and polymerization products thereof. The plasticizer that finds usefulness in the present invention can be any number of different plasticizers but the inventors have discovered that mineral oil such as Kaydol manufactured by Sonneborn, Inc., is particularly useful in the present invention. Benzoflex 9-88, a dipropylene glycol dibenzoate, and Benzoflex 352, 1,4-cyclohexanedimethanol dibenzoate, both manufactured by Velsicol, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications). In an embodiment in which polyethylene glycol is used as the base polymer, it has been found that the inclusion of a plasticizer increases the speed with which the color change occurs.

It should be understood that other optional additives may be incorporated into the adhesive composition of the present invention in order to modify particular physical properties. These may include, for example, such materials as inert colorants, e.g., titanium dioxide, and fillers. Typical fillers include talc, calcium carbonate, clay silica, mica, wollastonite, feldspar, aluminum silicate, alumina, hydrated alumina, glass microspheres, ceramic microspheres, thermoplastic microspheres, baryte and wood flour.

In addition, a wax may also be added in the composition, in the amount of about 1% to 50% by weight and preferably in the amount of about 5% to 40% by weight.

The hot melt adhesive composition of the present invention may be formulated using any of the techniques known in the art. A representative example of the prior art mixing procedure involves placing all the components, except the base polymer and the wetness indicator, in a jacketed mixing kettle equipped with a rotor, and thereafter raising the temperature of the mixture to melt the contents. It should be understood that the precise temperature to be used in this step would depend on the melting points of the particular ingredients. The polymers are subsequently introduced to the kettle under agitation and the mixing is allowed to continue until a consistent and uniform mixture is formed. Finally, the pH indicating agent is added, preferably after reducing the temperature as needed to protect the pH indicating agent and mixing is terminated when the wetness indicator has become completely dissolved in the mixture. The contents of the kettle are protected with inert gas such as carbon dioxide and nitrogen during the entire mixing process.

The resulting hot melt wetness indicator may then be applied to substrates using a variety of coating techniques. Examples include hot melt slot die coating, hot melt wheel coating, hot melt roller coating, melt-blown coating and spiral spray coating. In a preferred embodiment, the hot melt adhesive is coated onto a substrate using slot-die having 1-5 mm wide nozzles to produce a coated pattern having multiple wetness indicator stripes on the back sheet.

The adhesive composition of the present invention may be used in a number of nonwoven absorbent articles applications such as, for example, in disposable nonwoven infant and young child diapers, training pants, adult incontinent pads and briefs, etc. Such hygiene articles include a fluid-impervious back sheet having an inner surface, a nonwoven top sheet, and an absorbent core disposed between the back sheet and the top sheet. A hot melt wetness indicator composition of the present invention is applied to and, upon cooling, is bonded to the inner surface of the back sheet and in contact with the absorbent core such that, upon insult of the absorbent core with urine, the urine contacts the hot melt wetness indicator. The hot melt wetness indicator may serve to further bond the back sheet to the absorbent core.

The hot melt wetness indicator composition includes a non halogen-containing pH indicator that changes color when wet. By the term "wet" or "wetted," it is meant that the adhesive comes into contact with a water-based fluid such as urine, saline solution, blood, mucous and other bodily exudates, as well as water itself.

Based on the Examples below, it is submitted that the use of nitrazine yellow would serve adequately in any known hot melt wetness indicating formulations fitting within the compositional description of the present invention, namely a hot melt wetness indicator composition comprising: about 1 to about 80% by weight of a base polymer; about 15 to about 75% by weight of a tackifier; and a pH adjuster in an amount sufficient to cause the pH of the composition to be less than 6, preferably between 4 and 6, more preferably between 5 and 6, and most preferably between 5.5 and 6. Such formulations include those set forth in the examples of U.S. Pat. No. 8,828,271 and EP 1 330 272. Those formulations containing polyethylene glycol may lead to purple upon insult.

Aspects of the Invention

Aspect 1. A hot melt wetness indicator composition comprising:
about 1 to about 80% by weight of a base polymer;
about 15 to about 75% by weight of a tackifier;
a pH adjuster in an amount sufficient to cause the pH of the composition to be less than 6, preferably between 4 and 6, more preferably between 5 and 6, and most preferably between 5.5 and 6; and
about 0.01 to about 5% by weight of a pH indicating agent consisting of nitrazine yellow.

Aspect 2. The composition of Aspect 1, wherein:
the base polymer is present in an amount between about 1 and about 45% by weight, preferably between about 1% and 40% by weight;
the tackifier is present in an amount between about 20 and about 70% by weight, preferably between about 20% and about 50% by weight;
the pH adjuster is present in an amount between about 5 and about 55% by weight, preferably between about 10% and about 50% by weight, and most preferably between about 19 and about 43% by weight; and
the pH indicating agent is present in an amount between about 0.04 and about 2.5% by weight, preferably between about 0.05% and about 1.5% by weight, most preferably between about 0.07% and about 1% by weight.

Aspect 3. The composition of Aspects 1 or 2, wherein, wherein said base polymer is water soluble.

Aspect 4. The composition of any of Aspects 1 or 2, wherein the base polymer is selected from the group consisting of ethylene-vinyl-acetate (EVA), styrene-isoprene-styrene (SIS) block copolymer, styrene-butadiene-styrene (SBS) block copolymer, styrene-ethylene-butylene-styrene (SEBS) block copolymer, styrene-ethylene/ethylene-propylene-styrene (SEEPS) block copolymer, high density polyethylene, low density polyethylene, chemically modified polyethylene, sulfonated polyesters, polyvinylpyrrolidone, polyvinylpyrrolidone/vinyl acetate copolymer, amorphous polyalphaolefins, ethylene/styrene interpolymers (ESI), metallocene catalyzed APAOs, polyvinyl methyl ether, and polyethylene glycol and mixtures thereof.

Aspect 5. The composition of any of Aspects 1 or 2, wherein the base polymer comprises polyethylene glycol.

Aspect 6. The composition of any of Aspects 1 or 2, wherein said base polymer consists of polyethylene glycol.

Aspect 7. The composition of Aspects 5 or 6, wherein the base polymer is present in an amount of between about 10 and about 55% by weight, preferably between about 20 and about 45% by weight, and most preferably between about 25 and about 40% by weight.

Aspect 8. The composition of any of Aspects 1-7, wherein said tackifier is selected from the group consisting of natural rosin, modified rosin, hydrogenated rosin, polyterpene resins, copolymers of natural terpenes, terpolymers of natural terpenes, phenolic modified terpene resins, oligomeric amide ester resins, aliphatic petroleum hydrocarbon resins, aromatic hydrocarbon resins, and hydrogenated derivatives of said aromatic hydrocarbon resins and mixtures thereof.

Aspect 9. The composition of any of Aspects 1-7, wherein said tackifier is selected from the group consisting of hydrogenated rosin, aromatic hydrocarbon resins, and hydrogenated derivatives of said aromatic hydrocarbon resins, and mixtures thereof.

Aspect 10. The composition of any of Aspects 1-9 further comprising a surfactant in an amount of between about 1% and about 30% by weight, preferably in an amount of between about 4 and 15% by weight.

Aspect 11. The composition of Aspect 10, wherein the said surfactant is a nonionic surfactant, a cationic surfactant, or an anionic surfactant.

Aspect 12. The composition of Aspect 11, where the surfactant is the nonionic surfactant and is selected from the group consisting of alkyl amines and amides, alkanoamines and amides, amine oxides, ethoxylated fatty alcohols, ethoxylated fatty acids, ethoxylated alkylphenols, ethoxylated amines and amides, ethoxylated fatty esters and oils, glycerol fatty esters and their ethoxylated derivatives, sorbitan derivatives, sucrose esters and glucose esters and their derivatives.

Aspect 13. The composition of any of Aspects 1-12 further comprising a plasticizer in an amount of between about 1% and about 15% by weight, preferably in an amount of between about 1 and 10% by weight, and most preferably in the amount of about 1% to 7% by weight.

Aspect 14. The composition of Aspect 13, wherein said plasticizer is a water insoluble plasticizer.

Aspect 15. The composition of any of Aspects 1-14 further comprising a wax.

Aspect 16. The composition of any of Aspects 1-15 further comprising a stabilizer or an antioxidant.

Aspect 17. The composition of any of Aspects 1-16 further comprising a filler selected from the group consisting of talc, calcium carbonate, clay silica, mica, wollastonite, feldspar, aluminum silicate, alumina, hydrated alumina, glass microspheres, ceramic microspheres, thermoplastic microspheres, baryte, and wood flour.

Aspect 18. The composition of any of Aspects 1-17, wherein the pH adjuster is selected from the group consisting of glycolic acid, citric acid, lactic acid, ascorbic acid, oxalic acid, maleic acid, tartaric acid, salicylic acid, palmitic acid, stearic acid, and isostearic acid, and mixtures thereof.

Aspect 19. The composition of any of Aspects 1-17, wherein the pH adjuster is selected from the group consisting of stearic acid, isostearic acid, and mixtures thereof.

Aspect 20. A hygiene article comprising:
a fluid-impervious back sheet having an inner surface, a nonwoven top sheet, and an absorbent core disposed between the back sheet and the top sheet; and
a hot melt wetness indicator bonded to the inner surface of the back sheet and in contact with the absorbent core such that, upon insult of the absorbent core with urine, the urine contacts the hot melt wetness indicator, wherein the hot melt wetness indicator comprises:
about 1 to about 80% by weight of a base polymer;
about 15 to about 75% by weight of a tackifier;
a pH adjuster in an amount sufficient to cause the pH of the composition to be less than 6, preferably between 4 and 6, more preferably between 5 and 6, and most preferably between 5.5 and 5; and
about 0.01 to about 5% by weight of a pH indicating agent consisting of nitrazine yellow.

EXAMPLES

The following examples demonstrate several aspects of certain preferred embodiments of the present invention, and are not to be construed as limitations thereof.

Four formulations (referred to as formulations 1(a) through 1(d)) were prepared and the test results are shown in FIGS. 1(a) to 1(d). The formulations were as follows:

Formulation 1(a)—Polyethylene glycol having a molecular weight of about 20,000 daltons was used as the sole base polymer in an amount of 30% by weight; a blend of a hydrogenated rosin and an aromatic hydrocarbon resin was used use as the tackifier in an amount of 49% by weight; a blend of stearic (18%) and isostearic acid (2%) was used as the pH adjuster in an amount of 20% by weight; an antioxidant was used; and nitrazine yellow was used as the pH indicating agent in an amount of 0.18% by weight.

Formulation 1(b) had a base polymer other than polyethylene glycol; a tackifier; stearic acid as the pH adjuster; an antioxidant; a surfactant; and nitrazine yellow in an amount of 0.34% by weight.

Formulation 1(c) was similar to Example 8 of U.S. Pat. No. 8,828,271 except that it did not include a fluorescing agent but did include nitrazine yellow. In particular, formulation 1(c) included 28% by weight Polyglycol 20000S as the sole base polymer; 43% by weight Sylvaros TP 2040 as the tackifier; 8% by weight Benzoflex 9-88 as a plasticizer; 20% by weight Century 1224 as a pH adjuster; and nitrazine yellow in an amount of 0.2% by weight.

Formulation 1(d) was similar to Example 9 of U.S. Pat. No. 8,828,271 except that it did not include a fluorescing agent and did include nitrazine yellow. In particular, formulation 1(d) included 36% by weight Polyglycol 20000S as the sole base polymer; 35% by weight Sylvaros TP 2040 as the tackifier; 13% by weight Benzoflex 352 as a plasticizer; 20% by weight Century 1224 as a pH adjuster; and nitrazine yellow in an amount of 0.2% by weight.

Century 1224 is a saturated fatty acid product containing approximately 70 percent C18 stearic acid, with typically 23 percent methyl-branched C18 saturated acids.

Polyglykol 20000S is a polyethylene glycol with a mean molecular weight of 20000. It is a solid in flake form.

Silvaros TP 2040 is a terpene phenol resin used as a tackifier.

Benzoflex 9-88 is a high solvating plasticizer.

Benzoflex 352 is a solid plasticizer having a melt point of 118° C.

Nitrazine yellow is a pH indicator dye. Nitrazine indicates pH in the range of 4.5 to 7.5 and is usually used as the disodium salt.

Coated laminates were made by coating 25 gsm of the formulated, molten (90.5° C.) hot melt wetness indicator to breathable polymer film, BR-149, using a continuous 5 mm wide slot nozzle. The indicating strip on breathable film was then joined at a line speed of 100 fpm to a release liner.

Humidity resistance on formulation 1(a) and 1(b) was tested by stapling a section of each coated condition (25 gsm) to a white board and put in a humidity chamber at 40° C. and 80% relative humidity which was inspected for any changes in color. Both formulations showed stable color over three weeks.

Color change rate was tested by dropping Sensitive Eyes® (from Bausch & Lomb, Inc.) saline solution on the coated, fully cooled laminate and timing how long until color change was noticeable and the time for complete color change. The test was then repeated using a new, dry portion of the coated laminate and tested with a synthetic urine solution. The results are shown in FIGS. 1(a) to 1(d). As can be seen, the strip having formulation 1(a) went from yellow to purple; the strip having formulation 1(b) went from essentially colorless to blue; the strip having formulation 1(c) went from pale yellow to dull blue; and the strip having formulation 1(d) went from pale yellow to dull blue. The results of the time to color change were less than 2 minutes. Preferred embodiments can change colors instantaneously.

Color was determined via software. A photo was taken both initially (one day after the laminates were made) and after 5 minutes after addition of the saline solution. Utilizing publically available software from Pantone LLC (https://www.pantone.com/color-finder), colors were best matched/assigned a pantone color. The website allows users to input a color via sRGB, Hex, or CMYK nomenclature to find the best match. A representative sRGB color was determined from the photo depicted in FIGS. 1(a) to 1(d) and matched with a corresponding Pantone. The classification of the color changes can be seen below in Table 1. The color at the 'start' is an average of the entire strip where the hot melt wetness indicator was applied. The color 'after' is an average of the darkened portion corresponding to where the saline solution drops were disposed, excluding the edges of the drops where a noticeable change in the color of the drops occurs.

TABLE 1

| | Start | | After 5 min saline | |
| --- | --- | --- | --- | --- |
| | Visual | Pantone Match | Visual | Pantone Match |
| (a) | Yellow | Pantone P 8-5 U | Purple | Pantone 19-3728 TCX Grape |
| (b) | Colorless | Pantone 2310 C | Blue | Pantone 3597 CP |
| (c) | Yellow | Pantone 9-10 U | Pale blue | Pantone P 173-9 C |
| (d) | Yellow | Pantone 16-11 C | Pale blue | Pantone 108-16 U |

Where a range of values is provided, it is understood that each intervening value, and any combination or sub-combination of intervening values, between the upper and lower limit of that range and any other stated or intervening value in that stated range, is encompassed within the range of values recited. In addition, the invention includes a range of a constituent which is the lower limit of a first range and an upper limit of a second range of that constituent. Furthermore, whenever a constituent is discussed herein (such as a base polymer or a tackifier), reference to "a" constituent encompasses just a single such constituent, blends of different grades of that constituent, or blends of different types of that constituent.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue or prior invention.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

We claim:

1. A hot melt wetness indicator composition comprising:
   about 10 to about 80% by weight of a base polymer, wherein the base polymer comprises polyethylene glycol in an amount of at least 10% by weight;
   about 15 to about 75% by weight of a tackifier;
   a pH adjuster in an amount sufficient to cause the pH of the composition to be less than 6; and
   about 0.01 to about 5% by weight of a pH indicating agent consisting of nitrazine yellow, wherein the composition does not comprise a permanent dye.

2. The composition of claim 1, wherein:
   the base polymer is present in an amount between about 10 and about 45% by weight;
   the tackifier is present in an amount between about 20 and about 70% by weight;
   the pH adjuster is present in an amount between about 5 and about 55% by weight; and
   the pH indicating agent is present in an amount between about 0.04 and about 2.5% by weight.

3. The composition of claim 1, wherein said base polymer consists of polyethylene glycol.

4. The composition of claim 3, wherein said base polymer is present in an amount of between about 10 and about 55% by weight.

5. The composition of claim 1, wherein said tackifier is selected from the group consisting of natural rosin, modified rosin, hydrogenated rosin, polyterpene resins, copolymers of natural terpenes, terpolymers of natural terpenes, phenolic modified terpene resins, oligomeric amide ester resins, aliphatic petroleum hydrocarbon resins, aromatic hydrocarbon resins, and hydrogenated derivatives of said aromatic hydrocarbon resins and mixtures thereof.

6. The composition of claim 1, wherein said tackifier is selected from the group consisting of hydrogenated rosin, aromatic hydrocarbon resins, and hydrogenated derivatives of said aromatic hydrocarbon resins, and mixtures thereof.

7. The composition of claim 1 further comprising a surfactant in an amount of between about 1% and about 30% by weight.

8. The composition of claim 7, wherein said surfactant is a nonionic surfactant, a cationic surfactant, or an anionic surfactant.

9. The composition of claim 8, where the surfactant is the nonionic surfactant and is selected from the group consisting of alkyl amines and amides, alkanoamines and amides, amine oxides, ethoxylated fatty alcohols, ethoxylated fatty acids, ethoxylated alkylphenols, ethoxylated amines and amides, ethoxylated fatty esters and oils, glycerol fatty esters and their ethoxylated derivatives, sorbitan derivatives, sucrose esters and glucose esters and their derivatives.

10. The composition of claim 1 further comprising a plasticizer in an amount of between about 1% and about 15% by weight.

11. The composition of claim 10, wherein said plasticizer is a water insoluble plasticizer.

12. The composition of claim 1 further comprising a wax.

13. The composition of claim 1 further comprising a stabilizer or an antioxidant.

14. The composition of claim 1 further comprising a filler selected from the group consisting of talc, calcium carbonate, clay silica, mica, wollastonite, feldspar, aluminum silicate, alumina, hydrated alumina, glass microspheres, ceramic microspheres, thermoplastic microspheres, baryte, and wood flour.

15. The composition of claim 1, wherein the pH adjuster is selected from the group consisting of glycolic acid, citric acid, lactic acid, ascorbic acid, oxalic acid, maleic acid, tartaric acid, salicylic acid, palmitic acid, stearic acid, and isostearic acid, and mixtures thereof.

16. The composition of claim 1, wherein the pH adjuster is selected from the group consisting of stearic acid, isostearic acid, and mixtures thereof.

17. A hot melt wetness indicator composition comprising:
   about 1 to about 80% by weight of a base polymer, wherein said base polymer is selected from the group consisting of ethylene-vinyl-acetate (EVA), styrene-isoprene-styrene (SIS) block copolymer, styrene-butadiene-styrene (SBS) block copolymer, styrene-ethylene-butylene-styrene (SEBS) block copolymer, styrene-ethylene/ethylene-propylene-styrene (SEEPS) block copolymer, high density polyethylene, low density polyethylene, chemically modified polyethylene, sulfonated polyesters, polyvinylpyrrolidone, polyvinylpyrrolidone/vinyl acetate copolymer, amorphous polyalphaolefins, ethylene/styrene interpolymers (ESI), metallocene catalyzed APAOs, and polyvinyl methyl ether, and mixtures thereof;
   about 15 to about 75% by weight of a tackifier;
   a pH adjuster in an amount sufficient to cause the pH of the composition to be less than 6; and
   about 0.01 to about 5% by weight of a pH indicating agent consisting of nitrazine yellow, wherein the composition does not comprise a permanent dye.

18. The composition of claim 17, wherein said base polymer is water soluble.

19. The composition of claim 17, wherein:
   the base polymer is present in an amount between about 1 and about 45% by weight;
   the tackifier is present in an amount between about 20 and about 70% by weight;
   the pH adjuster is present in an amount between about 5 and about 55% by weight; and
   the pH indicating agent is present in an amount between about 0.04 and about 2.5% by weight.

20. The composition of claim 17 further comprising a surfactant in an amount of between about 1% and about 30% by weight.

21. A hygiene article comprising:
   a fluid-impervious back sheet having an inner surface, a nonwoven top sheet, and an absorbent core disposed between the back sheet and the top sheet; and a hot melt wetness indicator bonded to the inner surface of the back sheet and in contact with the absorbent core such that, upon insult of the absorbent core with urine, the urine contacts the hot melt wetness indicator, wherein the hot melt wetness indicator comprises:

about 10 to about 80% by weight of a base polymer, wherein the base polymer comprises polyethylene glycol in an amount of at least 10% by weight;

about 15 to about 75% by weight of a tackifier;

a pH adjuster in an amount sufficient to cause the pH of the indicator to be less than 6; and about 0.01 to about 5% by weight of a pH indicating agent consisting of nitrazine yellow, wherein the hot melt wetness indicator does not comprise a permanent dye.

* * * * *